US012582295B2

(12) United States Patent
Suwa

(10) Patent No.: US 12,582,295 B2
(45) Date of Patent: Mar. 24, 2026

(54) ENDOSCOPE TUBULAR CONNECTOR AND ENDOSCOPE

(71) Applicant: OLYMPUS CORPORATION, Tokyo (JP)

(72) Inventor: Takahiro Suwa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 446 days.

(21) Appl. No.: 17/891,216

(22) Filed: Aug. 19, 2022

(65) Prior Publication Data

US 2022/0386855 A1      Dec. 8, 2022

Related U.S. Application Data

(63) Continuation of application No. PCT/JP2020/009789, filed on Mar. 6, 2020.

(51) Int. Cl.
A61B 1/00          (2006.01)
A61B 1/005         (2006.01)
A61B 1/012         (2006.01)

(52) U.S. Cl.
CPC ...... A61B 1/00128 (2013.01); A61B 1/00119 (2013.01); A61B 1/0055 (2013.01)

(58) Field of Classification Search
CPC ............ A61B 1/00128; A61B 1/00119; A61B 1/0055; A61B 1/00101; A61B 1/0008; A61B 1/012
USPC ........................................................ 600/142
See application file for complete search history.

(56) References Cited

U.S. PATENT DOCUMENTS

| | | | | |
|---|---|---|---|---|
| 4,967,732 A * | 11/1990 | Inoue | ................. | A61B 1/00137 |
| | | | | 600/149 |
| 5,261,391 A | 11/1993 | Inoue | | |
| 5,735,793 A * | 4/1998 | Takahashi | .......... | A61B 1/00128 |
| | | | | 600/153 |
| 2009/0093679 A1 * | 4/2009 | Suigetsu | ............ | A61B 1/00128 |
| | | | | 600/139 |
| 2009/0171158 A1 * | 7/2009 | Matsuo | .............. | G02B 23/2476 |
| | | | | 600/139 |

(Continued)

FOREIGN PATENT DOCUMENTS

| | | |
|---|---|---|
| JP | H02-191423 A | 7/1990 |
| JP | H05-020706 U | 3/1993 |

(Continued)

OTHER PUBLICATIONS

International Search Report dated Apr. 28, 2020 received in PCT/JP2020/009789.

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

An endoscope tubular connector includes: a connection joint including a through-hole; and a tubular portion that is formed of a material softer than the connection joint and that has one end arranged in the through-hole of the connection joint. The through-hole of the connection joint and a through-hole of the tubular portion are formed such that the through-holes are connected to each other, and an outer circumference of the tubular portion is arranged on an inner side with respect to an inner circumference of the connection joint.

19 Claims, 6 Drawing Sheets

(56)        References Cited

U.S. PATENT DOCUMENTS

2012/0271108 A1*  10/2012  Hoshino  ............  A61B 1/00091
                                                                     600/139
2013/0131453 A1*   5/2013  Imai  ..................  A61B 1/00091
                                                                     600/156
2013/0150667 A1*   6/2013  Mitamura  ..........  A61B 1/00064
                                                                     600/104
2016/0213225 A1*   7/2016  Sato  ........................  A61B 1/018
2016/0374537 A1*  12/2016  Chae  ..................  A61B 1/00089
                                                                     600/127
2017/0010458 A1*   1/2017  Nishijima  ..........  G02B 23/2476
2020/0154981 A1*   5/2020  Mankowski  .......  A61B 1/00103
2021/0109311 A1*   4/2021  Sakai  .................  A61B 1/00128

FOREIGN PATENT DOCUMENTS

JP        H05-49593  A        3/1993
JP        H05-293075  A      11/1993
JP        2006006761  A    *  1/2006
JP        2017-209278  A     11/2017
WO        2013/035379  A1     3/2013

* cited by examiner

ENDOSCOPE TUBULAR CONNECTOR AND ENDOSCOPE

CROSS-REFERENCE TO RELATED APPLICATION

This application is a continuation of International Application No. PCT/JP2020/009789, filed on Mar. 6, 2020, the entire contents of which are incorporated herein by reference.

BACKGROUND

1. Technical Field

The present disclosure relates to an endoscope tubular connector and an endoscope.

2. Related Art

An insertion portion of an endoscope is usually inserted into a subject, such as a patient, and thereby the endoscope acquires data of internal images of the subject using an imaging device and provides treatment using a treatment tool, or the like. In a treatment tool channel into which a treatment tool is inserted, a tubular portion made of resin is attached via a connection joint to an opening of a distal end portion of an insertion portion of an endoscope and the tubular portion is put on the connection joint on a proximal end side and the tubular portion is joined by resin or is bound with a thread to be prevented from dropping off (refer to Japanese Laid-open Patent Publication No. 2017-209278).

SUMMARY

In some embodiments, an endoscope tubular connector includes: a connection joint including a through-hole; and a tubular portion that is formed of a material softer than the connection joint and that has one end arranged in the through-hole of the connection joint. The through-hole of the connection joint and a through-hole of the tubular portion are formed such that the through-holes are connected to each other, and an outer circumference of the tubular portion is arranged on an inner side with respect to an inner circumference of the connection joint.

In some embodiments, an endoscope includes: a distal end portion that is provided at a distal end part of an insertion portion and that has a through-hole; a bendable part that is provided on a proximal end side of the distal end part and that is bendable according to a bending operation; a connection joint that has a first end connected to the distal end portion and a second end arranged in the bendable part and that has a through-hole connected to the through-hole of the distal end portion; and a tubular portion that is formed cylindrically, that is provided in the insertion portion, and that has one end connected to the second end of the connection joint to be connected to the through-hole of the connection joint. An outer circumference of the tubular portion is arranged on an inner side with respect to an inner circumference of the connection joint.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
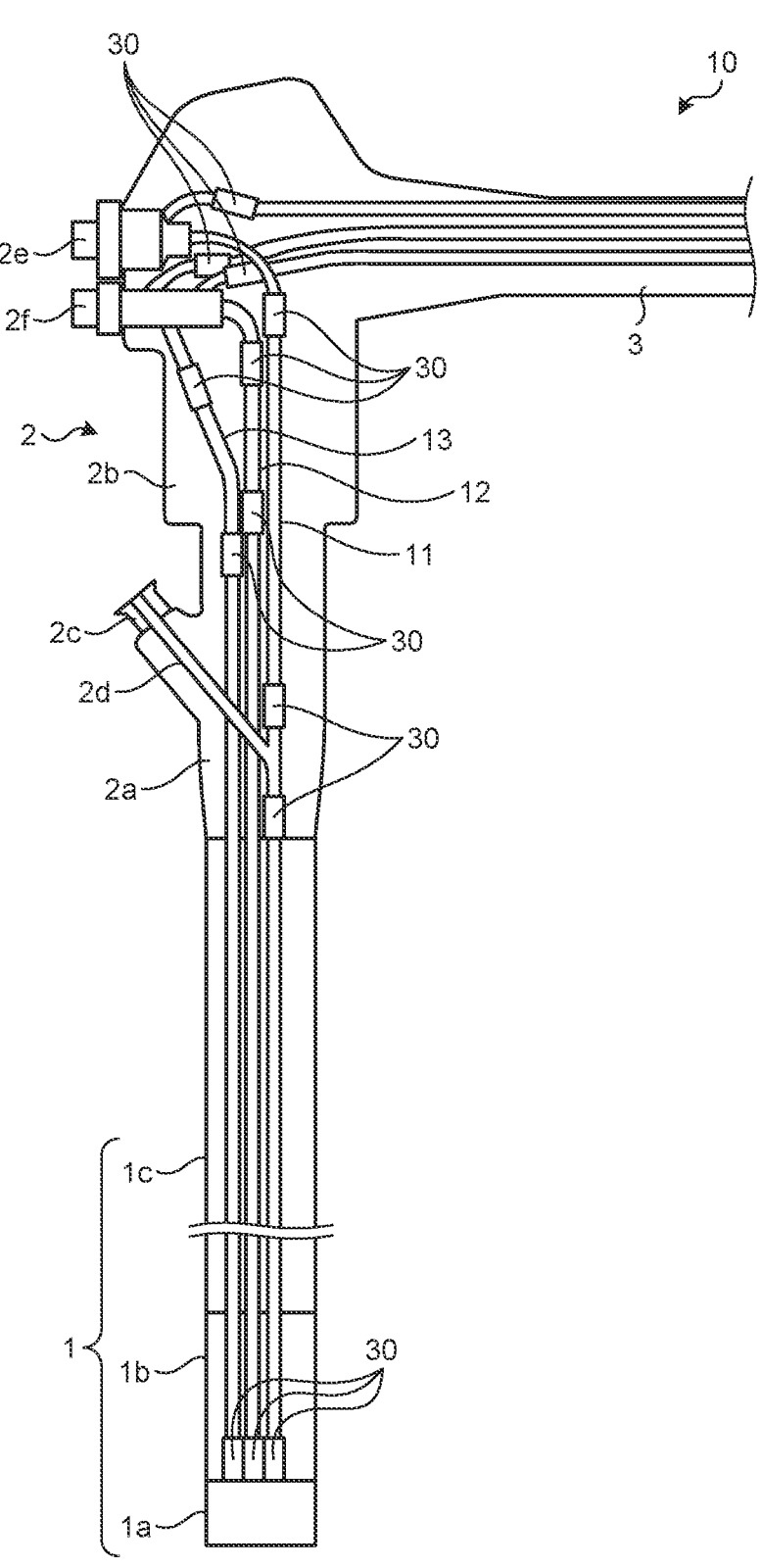
FIG. 1 is a schematic view of an endoscope according to a first embodiment of the disclosure.

In the following description, an endoscope system including a distal end part of an endoscope will be described as a mode for carrying out the disclosure ("embodiment" below). The embodiments do not limit the disclosure. In the description of the drawings, the same parts are denoted by the same reference numerals. Note that the drawings are schematic and the relation between the thickness and width of each member, the ratio of each member, etc., are different from actual ones. The drawings contain parts whose sizes and ratios differ among the drawings. Note that the same components are denoted by the same reference numbers through the description of the embodiments.

First Embodiment

FIG. 1 is a schematic view of an endoscope 10 according to a first embodiment of the disclosure. As illustrated in FIG. 1, the endoscope 10 according to the first embodiment includes an insertion portion 1 configured to be inserted into a subject, an operation unit 2 that is on a side of a proximal end of the insertion portion 1 and that is held by a practitioner, and a universal cord 3 that is flexible and that extends from the operation unit 2.

The insertion portion 1 is realized using a light guide cable, an electronic cable, an optical fiber, various channels, etc. The insertion portion 1 includes a distal end part 1a including an observation unit, an illuminator, and openings for the various channels, a bendable part 1b that flexibly bends and that consists of a plurality of bending members, and a flexible tube 1c that is flexible and that is arranged on the side of a proximal end part of the bendable part 1b. The distal end part 1a is provided with a light guide cable that illuminates the inside of the subject, an imaging unit that captures internal images of the subject, and an opening into which a treatment channel is inserted.

The operation unit 2 includes a body 2a and a holding part 2b that an operator who operates the endoscope 10 holds.

The body 2a is provided with a treatment tool insertion part 2c via which a treatment tool, such as biology forceps or a surgical laser, is inserted into the body cavity of the subject. A proximal end part of treatment tool channels 2d is connected to the treatment tool insertion part 2c. The treatment tool channel 2d is provided from the distal end part 1a to the flexible tube 1c. The treatment tool, such as biology forceps, is inserted from the treatment tool insertion portion 2c to the treatment tool channel 2d and is pushed to the opening of the distal end part 1a.

The holding part 2b is provided with a bending operator that is not illustrated in the drawing and that is for operating the bendable part 1b. The holding part is also provided with a suction switch 2e for a suction tube 11 and an air supply and water supply switch 2f for an air supply tube 12 and a water supply tube 13. The suction tube 11, the air supply tube 12 and the water supply tube 13 are provided from the distal end part 1a to the flexible tube 1c. The treatment tool channel 2d, the suction tube 11, the air supply tube 12 and the water supply tube 13 include an endoscope tubular connector 30 to which tubular portions, such as tubes, are connected via a connection joint.

Figure 2:
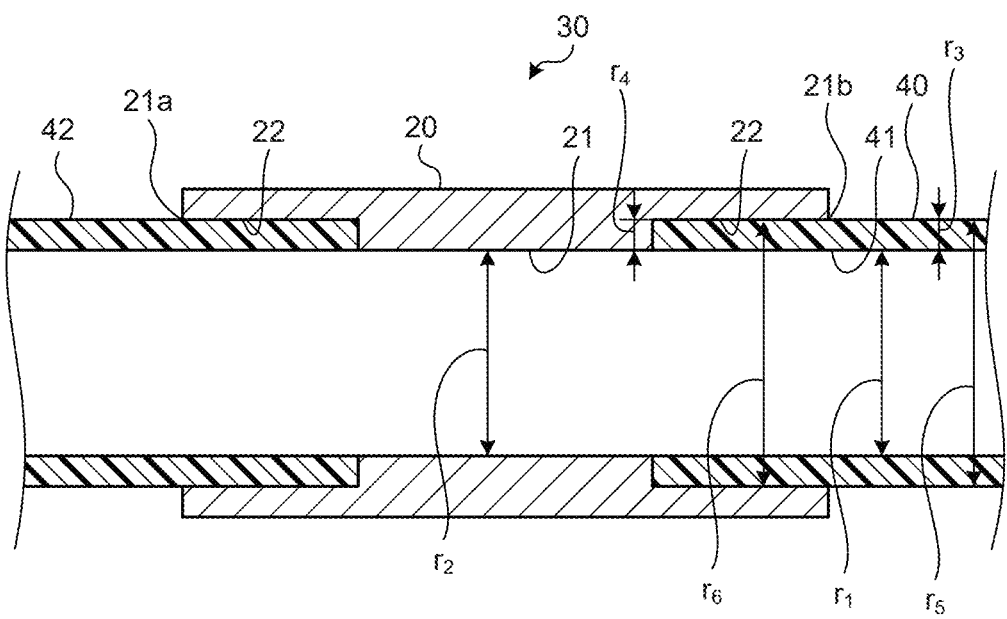
FIG. 2 is a cross-sectional view of an endoscope tubular connector that is used in the endoscope illustrated in FIG. 1.

FIG. 2 is a cross-sectional view of the endoscope tubular connector 30. The endoscope tubular connector 30 includes a connection joint 20 including a through-hole 21 and a tubular portion 40 that is formed of a material that is softer than the connection joint 20 and that has one end arranged in the through-hole 21 of the connection joint 20. The through-hole 21 is formed, penetrating through an opening 21a that is provided on a distal end side and an opening 21b that is provided on a proximal end side. The through-hole 21 of the connection joint 20 and a through-hole 41 of the tubular portion 40 are formed such that the through-hole 21 and the through-hole 41 are connected with each other and, on the inner circumference of an end of the connection joint 20 on which the tubular portion 40 is arranged, a step 22 whose inner diameter on the side of the end is larger than that on the side of the center along the axis of the axis of the through-hole 21 is provided.

The cross-sectional shapes of the through-hole 21 of the connection joint 20 and the through-hole 41 of the tubular portion 40 are circular; however, the cross-sectional shapes are not limited to this and they may be oval.

The tubular portion 40 is made of a material that is softer than the connection joint 20. The tubular portion 40 is bonded and fixed with its distal end surface being pushed against the step 22 of the connection joint 20. An inner diameter r1 of the tubular portion 40 is preferably equal to or smaller than an inner diameter r2 of the connection joint 20. Setting the inner diameter r1 of the tubular portion 40 at or under the inner diameter r2 of the connection joint 20 makes it possible to, when the treatment tool is inserted from the treatment tool insertion part 2c, prevent the treatment tool from getting stuck in the end of the connection joint 20. Similarly, a thickness r3 of the tubular portion 40 is preferably equal to or larger than a height r4 of the step 22 of the connection joint 20. Note that, because the tubular portion 40 consists of the material softer than the connection joint 20, even if the thickness r3 of the tubular portion 40 is set equal to or larger than the height r4 of the step 22 of the connection joint 20, the treatment tool tends not to get stuck in the tubular portion 40 when the treatment tool is pulled out of the treatment toll channel 2d; however, in view of ensuring the diameter of the treatment tool channel 2d for easy insertion and removal of the treatment tool, the thickness r3 of the tubular portion 40 is preferably equal to or smaller than 1.2 times the height r4 of the step 22 of the connection joint 20. An outer diameter r5 of the tubular portion 40 is preferably equal to or larger than an inner diameter r6 at the step 22 of the connection joint 20.

An outer circumferential surface of an end of the tubular portion 40 is bonded and fixed to the step 22 of the connection joint 20. An adhesive, or the like, may be used as the method of the bonding and fixing, and it is preferable that the surface of the step 22 be processed to have a rough surface to increase the strength of bonding to the tubular portion 40. Arranging the end of the tubular portion 40 on the step 22 of the connection joint 20 and thereafter at least any one of or both of pressurizing and heating the outer circumferential side from the direction of the through-hole 41 of the tubular portion 40 enable bonding and fixation of the tubular portion 40 and the connection joint 20. Alternatively, the tubular portion 40 may be directly mold on the step 22 of the connection joint 20 (metal insertion).

In the endoscope tubular connector 30 according to the first embodiment, it is possible to effectively prevent the treatment tool from getting stuck when being inserted or being removed and, because the tubular portion 40 is arranged in the connection joint 20, a small diameter of the treatment tool channel 2d is enabled. In view of a small diameter, the endoscope tubular connector 30 is preferably usable for the suction tube 11, the air supply tube 12 and the water supply tube 13 other than the treatment tool channel 2d.

Second Embodiment

Figure 3:
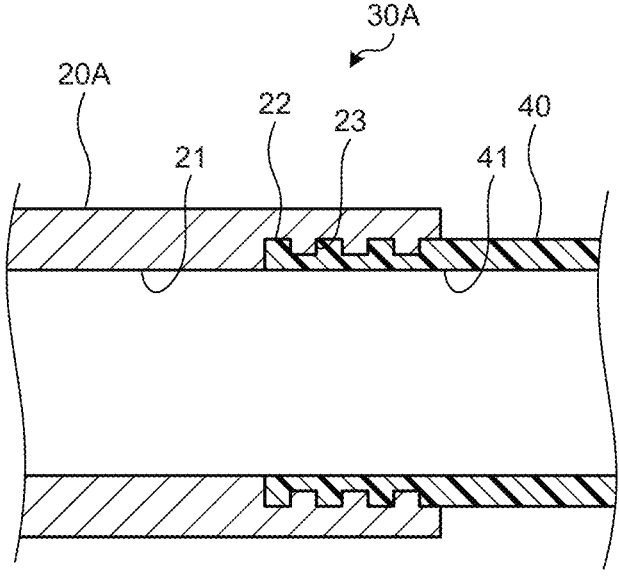
FIG. 3 is a cross-sectional view of an endoscope tubular connector according to a second embodiment of the disclosure.

FIG. 3 is a cross-sectional view of an endoscope tubular connector 30A according to a second embodiment of the disclosure. The endoscope tubular connector 30A has a convex portion 23 in the step 22 of a connection joint 20A.

A plurality of the convex portions 23 are formed in the step 22 of the connection joint 20A. The convex portion 23 may be cylindrical, prismatic, conical or pyramidal and the convex portion 23 is formed in a height smaller than that of the step 22. The convex portion 23 cuts into an outer circumferential surface of the tubular portion 40 and functions as a regulator that regulates dropping off of the tubular portion 40.

In the endoscope tubular connector 30A, after the end of the tubular portion 40 is arranged on the step 22 of the connection joint 20A, and thereafter at least any one of or both of a pressure and a heat is applied to an outer circumferential side from the direction of the through-hole 41 of the tubular portion 40, so that the convex portions 23 on the step 22 of the connection joint 20A cut into the outer circumferential surface of the tubular portion 40 and are bonded and fixed.

In the endoscope tubular connector 30A according to the second embodiment, providing the convex portions 23 on the step 22 makes it possible to effectively prevent the tubular portion 40 from dropping off. As in the first embodiment, it is possible to prevent the treatment tool from getting stacked when the treatment tool is inserted or removed and, because the tubular portion 40 is arranged in the connection joint 20A, a small diameter of the treatment tool channel 2d is enabled.

Figure 4:
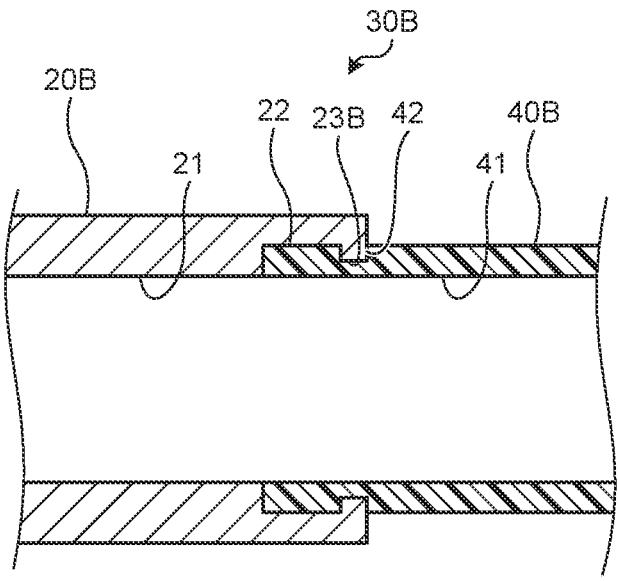
FIG. 4 is a cross-sectional view of an endoscope tubular connector according to a modification of the second embodiment of the disclosure.
Figure 5:
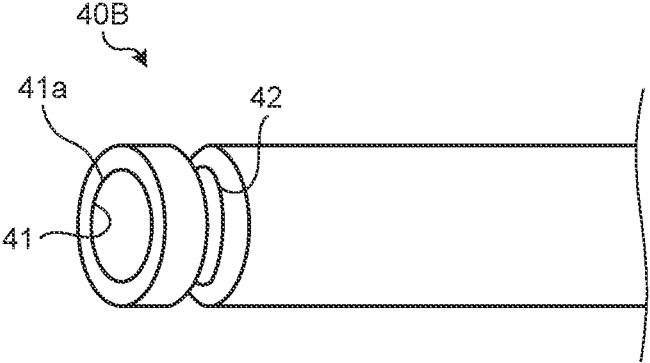
FIG. 5 is a perspective view of a tubular portion that is used in the endoscope tubular connector illustrated in FIG. 4.

In the second embodiment, the convex portions 23 functioning as the regulator are provided in the step of the connection joint 20A; however, the regulator is not limited to this. FIG. 4 is a cross-sectional view of an endoscope tubular connector 30B according to a modification of the second embodiment of the disclosure. FIG. 5 is a perspective view of a tubular portion 40B that is used in the endoscope tubular connector 30B illustrated in FIG. 4. In the endoscope tubular connector 30B, the regulator is provided in a connection joint 20B and the tubular portion 40B.

On a proximal end part of the step 22 of the connection joint 20B, a convex portion 23B is provided circumferentially. In the tubular portion 40B, a concave portion 42 is provided circumferentially. The tubular portion 40B is arranged such that the connection joint 20B, the convex portion 23B and the concave portion 42 are fitted together and is bonded and fixed.

In the modification of the second embodiment, providing the connection joint 20B and the tubular portion 40B with the convex portion 23B and the concave portion 42 that function as the regulator, respectively, fitting the convex portion 23B and the concave portion 42 together, and bonding and fixing the convex portion 23B and the concave portion 42 make it possible to effectively prevent the tubular portion 40B from dropping off.

Figure 6A:
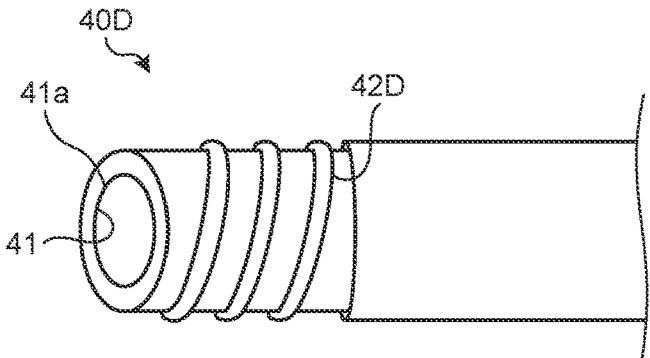
FIG. 6A is a perspective view of a tubular portion according to another modification of the second embodiment of the disclosure.
Figure 6B:
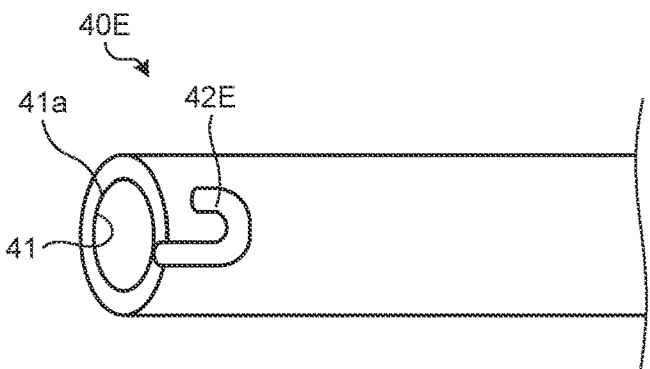
FIG. 6B is a perspective view of a tubular portion according to another modification of the second embodiment of the disclosure.

Examples of the regulator are not limited to the above-described one, and one that enables fitting and regulation on dropping off of the tubular portion may be used. FIGS. 6A and 6B is perspective views of tubular portions according to another modification of the second embodiment of the disclosure. The regulator may be screws to be engaged with each other or a claw-shaped groove. FIG. 6A illustrates a tubular portion 40D with an outer circumferential surface on which a male screw 42D is formed and, in that case, a female screw is formed on a step of a connection joint and the screws are engaged with each other and thus are able to serve as the regulator. FIG. 6B illustrates a tubular portion 40E with an outer circumferential surface on which a claw-shaped groove 42E is formed and, in that case, a claw-shaped convex portion is formed on a step of a connection joint and the groove 42E and the convex portion are fitted together and thus are able to serve as the regulator.

Third Embodiment

Figure 7:
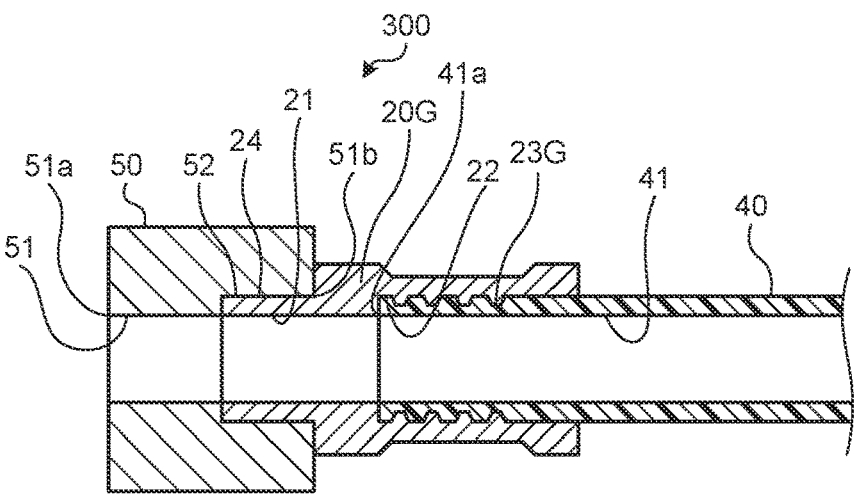
FIG. 7 is a cross-sectional view of an endoscope tubular connector according to a third embodiment of the disclosure.
Figure 8:
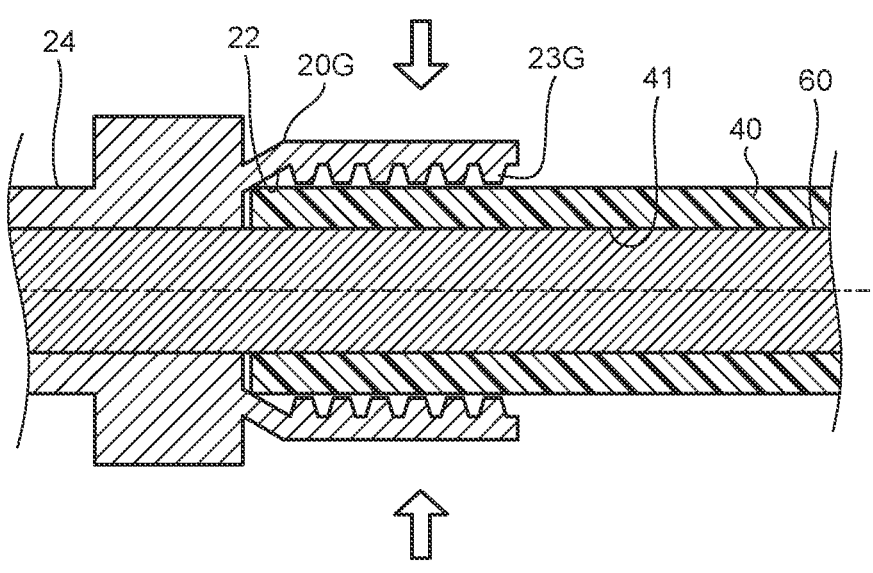
FIG. 8 is a diagram illustrating a method of manufacturing the endoscope tubular connector illustrated in FIG. 7.

FIG. 7 is a cross-sectional view of an endoscope tubular connector 300 according to a third embodiment of the disclosure. FIG. 8 is a diagram illustrating a method of manufacturing the endoscope tubular connector 300 illustrated in FIG. 7. The endoscope tubular connector 300 includes, in addition to a connection joint 20G and the tubular portion 40, a distal end portion 50 that is provided in the distal end part 1a of the insertion portion 1 and that has a through-hole 51. In the distal end portion 50, in addition to an opening for a treatment tool channel, an illuminator, an observation unit and openings for air supply and water supply are provided; however, illustration thereof is omitted in FIG. 7 and FIG. 8.

The distal end portion 50 has the through-hole 51 forming the treatment tool channel. The through-hole 51 is formed, penetrating through an opening 51a that is provided on a distal end side and an opening 51b that is provided on a proximal end side. On the proximal end side of the through hole 51, a fitting part 52 in which the connection joint 20G is fitted is formed.

A fitting part 24 is formed on an outer circumferential surface of the connection joint 20G on the distal end side, the fitting part 24 is inserted into the fitting part 52 of the distal end portion 50, and the distal end portion 50 and the connection joint 20 are bonded and fixed. In the step 22 in the through-hole 21 of the connection joint 20G on the proximal end side, as in the second embodiment, a plurality of convex portions 23G are formed.

As for the connection joint 20G and the tubular portion 40, as illustrated in FIG. 8, after the tubular portion 40 with a swage jig 60 being inserted into the through-hole 41 is arranged on the step 22 of the connection joint 20G on the proximal end side, the proximal end side on which the step 22 of the connection joint 20G is formed is pressed from an outer circumferential side and accordingly the convex portions 23G are cut into the outer circumferential surface of the tubular portion 40 and are fixed. After the pressing, the swage jig 60 is pulled out of the tubular portion 40. It is preferable that, for the press, the swage jig 60 be heated in view of increasing the strength of connection between the connection joint 20G and the tubular portion 40.

In the endoscope tubular connector 300 according to the third embodiment, it is possible to effectively prevent the treatment tool from getting stuck when being inserted or being removed and, because the tubular portion 40 is arranged in the connection joint 20, small diameter of the treatment tool channel 2d is enabled. Furthermore, setting the convex portions 23G on the step 22 makes it possible to effectively prevent the tubular portion 40 from dropping off. In view of a small diameter, the endoscope tubular connector 300 is preferably usable for the suction tube 11, the air supply tube 12 and the water supply tube 13 other than the treatment tool channel 2d.

Figure 9:
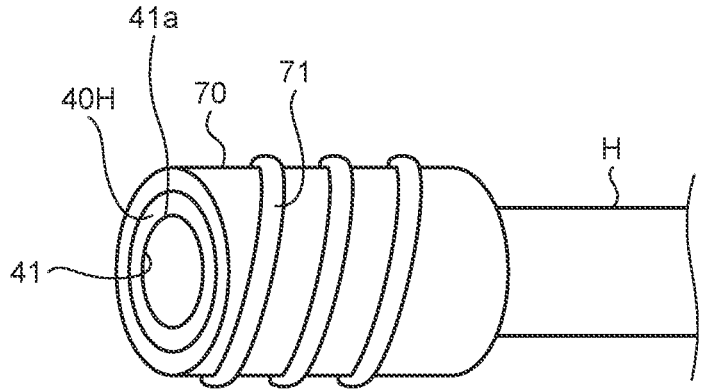
FIG. 9 is a perspective view of a tubular portion according to a modification of the third embodiment of the disclosure.

In the third embodiment, the proximal end side of the connection joint 20G in which the convex portions 23G are formed is pressed against the tubular portion 40 and accordingly the connection joint 20G and the tubular portion 40 are fixed; however, fixation of the connection joint and the tubular portion is not limited to this. FIG. 9 is a perspective view of a tubular portion 40H according to a modification of the third embodiment of the disclosure. A metal screw 70 is attached fixedly to the tubular portion 40H on the distal end side.

As illustrated in FIG. 9, the metal screw 70 in which a male screw 71 is formed is attached fixedly on the distal end side of the tubular portion 40H. The tubular portion 40H is directly molded in the metal screw 70 (metal insertion). A female screw is formed in a step of a connection joint not illustrated in the drawing and the female screw is engaged with the male screw 71 of the tubular portion 40H and accordingly the connection joint and the tubular portion 40H can be fixed. The female screw of the connection joint and the male screw 71 of the tubular portion 40H function as the regulator. In the modification, an effect similar to that of the third embodiment is enabled.

Fourth Embodiment

Figure 10:
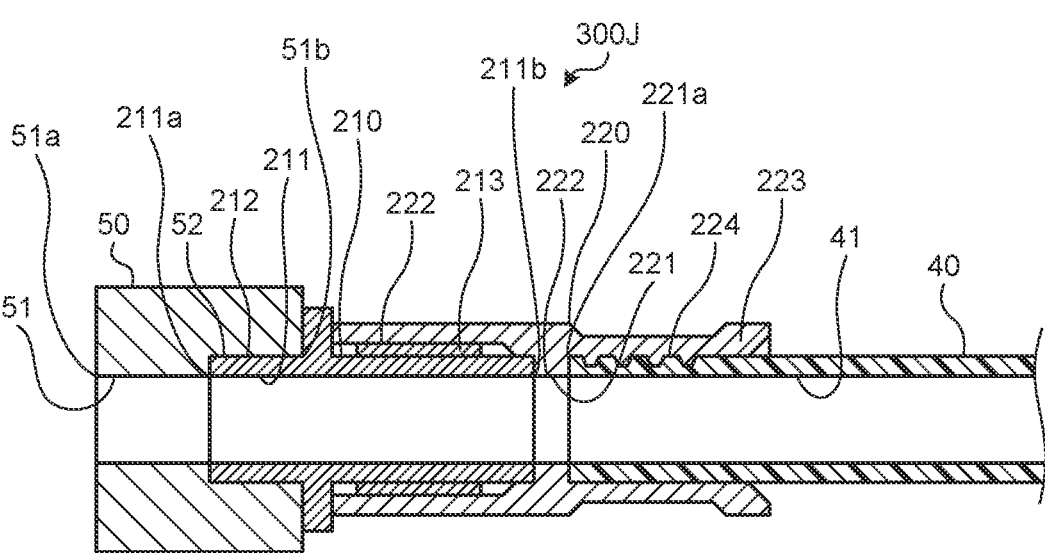
FIG. 10 is a cross-sectional view of an endoscope tubular connector according to a fourth embodiment of the disclosure.

FIG. 10 is a cross-sectional view of an endoscope tubular connector 300J according to a fourth embodiment of the disclosure. In the endoscope tubular connector 300J, a connection joint includes a first joint 210 that is fitted in the distal end portion 50 and a second joint 220.

The first joint 210 has a through-hole 211. The through-hole 211 is formed, penetrating through an opening 211a that is provided on a distal end side and an opening 211b that is provided on a proximal end side. A fitting part 212 is formed on a circumferential surface on the distal end side and a screw part 213 is formed on the outer circumferential surface on a proximal end side. The fitting part 212 is inserted into the fitting part 52 of the distal end portion 50 and is bonded and fixed to the distal end portion 50.

The second joint 220 has a through-hole 221, has a step 222 in which a screw part not illustrated in the drawing is formed on an inner circumference on the distal end side, and has a step 223 in which a plurality of convex portions 224 are formed on an inner circumferential surface on the proximal end side. The distal end side of the second joint 220 is screwed while being inserted into the proximal end side of the first joint 210. The tubular portion 40 is fixed on the proximal end side of the second joint 220.

In the treatment tool channel 2d, because the treatment tool is inserted and removed repeatedly, a crack, or the like, sometimes occurs in the tubular portion 40. In general, a distal end portion, a connection joint and a tubular portion are bonded and fixed tightly by an adhesive, detachment of the tubular portion 40 from the connection joint is not easy when the tubular portion 40 is replaced. In the fourth embodiment, the connection joint consists of the first joint 210 and the second joint 220 and, when the tubular portion 40 is replaced, the tubular portion 40 is detached together with the second joint 220. The first joint 210 and the second joint 220 are fixed by screwing and therefore they can be detached easily. The second joint 220 that is detached together with the tubular portion 40 may be replaced with the second joint 220 that is new or may be reused.

When the endoscope tubular connector of the disclosure is used as a treatment tool channel, insertion and removal of the treatment tool is easy and a small diameter is enabled.

According to the disclosure, it is possible to insert a treatment tool easily and a small diameter of an endoscope insertion portion is enabled.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope tubular connector comprising:
a connection joint including:
a first through-hole;
an inner step having a first inner diameter greater than a second inner diameter of the first through-hole; and
at least one cylindrical protrusion extending into the inner step, the at least one cylindrical protrusion having a cylindrical-ring shape with a third inner diameter between the first inner diameter and the second inner diameter;
a flexible tube having a first end arranged in the first through-hole of the connection joint, the flexible tube including:
a second through-hole fixed to the first through-hole; and
at least one groove separately formed from the at least one cylindrical protrusion and offset longitudinally from the first end, the at least one cylindrical protrusion being disposed in the at least one groove,
wherein an outer diameter of the flexible tube is arranged radially outward relative to the second inner diameter;
the inner step comprises a first inner step disposed at one end of the connection joint, the at least one cylindrical protrusion comprises at least one first cylindrical protrusion;
the connection joint includes a second inner step at an other end and at least one second cylindrical protrusion having a cylindrical ring shape, the second cylindrical protrusion being disposed at the second inner step; and
the flexible tube comprises a first flexible tube disposed at the one end; and

further comprising a second flexible tube disposed at the other end.

2. The endoscope tubular connector according to claim 1, wherein a first inner circumference of the first inner step corresponding to the one end of the connection joint is larger than a second inner circumference of the first inner step corresponding to a portion of the connection joint offset internally from the first end.

3. The endoscope tubular connector according to claim 1, wherein
cross-sectional shapes of both the first through-hole of the connection joint and the second through-hole of the first flexible tube are circular, and
an inner diameter of the first flexible tube is equal to or smaller than an inner diameter of the connection joint.

4. The endoscope tubular connector according to claim 1, wherein an outer circumferential surface of the first end of the first flexible tube is bonded and fixed to an inner circumferential surface of the first inner step of the connection joint.

5. The endoscope tubular connector according to claim 1, wherein the first tube flexible tube is made of a more flexible material than the connection joint.

6. An endoscope comprising:
a distal end portion provided at a distal end part of an insertion portion and that has a first through-hole;
a bendable part provided on a proximal end side of the distal end portion and that is bendable according to a bending operation;
a connection joint that has a first end connected to the distal end portion and a second end arranged in the bendable part and that has a second through-hole connected to the first through-hole of the distal end portion, the second through-hole having an inner step having a first inner diameter greater than a second inner diameter of the second through-hole; and
a flexible tube provided in the insertion portion, and that has a third end connected to the second end of the connection joint, the flexible tube having a third through-hole fixed to the second through-hole,
wherein an outer diameter of the flexible tube is arranged radially outward relative to the second inner diameter,
the connection joint having at least one cylindrical protrusion extending into the inner step, the at least one cylindrical protrusion having a cylindrical-ring shape with a third inner diameter between the first inner diameter and the second inner diameter; and
the flexible tube having at least one groove separately formed from the at least one cylindrical protrusion and offset longitudinally from the third end, the at least one cylindrical protrusion being disposed in the at least one groove.

7. The endoscope tubular connector according to claim 1, wherein
the at least one groove comprises at least one first groove,
the second flexible tube having at least one second groove offset longitudinally from a second end, and
the at least one second cylindrical protrusion of the second inner step being disposed in the at least one second groove offset longitudinally from the second end of the second flexible tube.

8. The endoscope tubular connector according to claim 1, wherein the first inner step has a longitudinal length, the at least one first cylindrical protrusion comprises a single first cylindrical protrusion, and a longitudinal length of the single first cylindrical protrusion is less than half of the longitudinal length of the first inner step.

9. The endoscope tubular connector according to claim 1, wherein, when the first and second through-holes are fixed to each other, the first inner diameter of the first inner step being constant over its longitudinal length other than for the at least one first cylindrical protrusion.

10. The endoscope according to claim 6, wherein the inner step comprises a first inner step disposed at one end of the connection joint, the at least one cylindrical protrusion comprises at least one first cylindrical protrusion;

the connection joint includes a second inner step at an other end and at least one second cylindrical protrusion having a cylindrical ring shape, the second cylindrical protrusion being disposed at the second inner step; and the flexible tube comprises a first flexible tube disposed at the one end; and further comprising a second flexible tube disposed at the other end.

11. The endoscope according to claim 10, wherein the at least one groove comprises at least one first groove, the second flexible tube having at least one second groove offset longitudinally from a second end, and the at least one second cylindrical protrusion of the second inner step being disposed in the at least one second groove offset longitudinally from the second end of the second flexible tube.

12. The endoscope according to claim 6, wherein the at least one cylindrical protrusion is formed at an end face of the connection joint.

13. The endoscope according to claim 6, wherein the inner step has a longitudinal length, the at least one protrusion comprises a single cylindrical protrusion, and a longitudinal length of the single cylindrical protrusion is less than half of the longitudinal length of the inner step.

14. The endoscope tubular connector according to claim 1, wherein the first and second through holes having concentric cylinder-shapes.

15. The endoscope tubular connector according to claim 14, wherein the first and second through holes having the same diameter cylinder-shapes.

16. The endoscope tubular connector according to claim 1, wherein an entire outer periphery of the at least one first cylindrical protrusion contacts with an entire inner periphery of the at least one groove.

17. The endoscope according to claim 6, wherein the first and second through holes having concentric cylinder-shapes.

18. The endoscope according to claim 17, wherein the first and second through holes having the same diameter cylinder-shapes.

19. The endoscope according to claim 6, wherein an entire outer periphery of the cylindrical protrusion contacts with an entire inner periphery of the groove.

* * * * *